(12) United States Patent
Banowski et al.

(10) Patent No.: US 8,883,130 B2
(45) Date of Patent: *Nov. 11, 2014

(54) TRANSPARENT ANTIPERSPIRANT GELS

(75) Inventors: Bernhard Banowski, Dusseldorf (DE); Nadine Buse, Hilden (DE); Marcus Claas, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/163,833

(22) Filed: Jun. 20, 2011

(65) Prior Publication Data

US 2011/0250160 A1 Oct. 13, 2011

Related U.S. Application Data

(63) Continuation of application No. PCT/EP2009/067623, filed on Dec. 21, 2009.

(30) Foreign Application Priority Data

Dec. 22, 2008 (DE) .......................... 10 2008 064 198

(51) Int. Cl.
| | | |
|---|---|---|
| *A61Q 15/00* | (2006.01) | |
| *A61K 8/28* | (2006.01) | |
| *A61K 8/26* | (2006.01) | |
| *A61K 8/06* | (2006.01) | |
| *A61K 8/894* | (2006.01) | |
| *A61K 8/893* | (2006.01) | |
| *A61K 8/39* | (2006.01) | |
| *A61K 8/37* | (2006.01) | |

(52) U.S. Cl.
CPC ........... *A61Q 15/00* (2013.01); *A61K 2800/262* (2013.01); *A61K 8/28* (2013.01); *A61K 8/064* (2013.01); *A61K 8/894* (2013.01); *A61K 8/06* (2013.01); *A61K 8/893* (2013.01); *A61K 8/39* (2013.01); *A61K 8/37* (2013.01)
USPC .................................. 424/65; 424/66; 424/68

(58) Field of Classification Search
None
See application file for complete search history.

(56) References Cited

U.S. PATENT DOCUMENTS

| | | | |
|---|---|---|---|
| 2,571,030 A | 10/1951 | Govett et al. | |
| 4,017,599 A | 4/1977 | Rubino | |
| 4,775,528 A | 10/1988 | Callaghan et al. | |
| 5,162,378 A * | 11/1992 | Guthauser | 514/785 |
| 5,429,816 A * | 7/1995 | Hofrichter et al. | 424/66 |
| 5,643,558 A * | 7/1997 | Provancal et al. | 424/66 |
| 6,010,688 A | 1/2000 | Shen | |
| 6,042,816 A | 3/2000 | Shen | |
| 6,245,325 B1 | 6/2001 | Shen | |
| 6,436,381 B1 | 8/2002 | Carrillo et al. | |
| 6,649,152 B2 | 11/2003 | Carrillo et al. | |
| 6,663,854 B1 | 12/2003 | Shen et al. | |
| 6,902,723 B2 | 6/2005 | Shen | |
| 6,923,952 B2 | 8/2005 | Allen et al. | |
| 7,105,691 B2 | 9/2006 | Holerca et al. | |
| 2004/0009133 A1 | 1/2004 | Kolodzik et al. | |
| 2004/0241196 A1* | 12/2004 | Popoff | 424/401 |
| 2006/0029624 A1* | 2/2006 | Banowski et al. | 424/401 |
| 2009/0304616 A1* | 12/2009 | Banowski et al. | 424/65 |

FOREIGN PATENT DOCUMENTS

| | | |
|---|---|---|
| DE | 102007059297 A1 | 7/2008 |
| GB | 2048229 A | 12/1980 |
| GB | 2299506 A | 10/1996 |
| WO | WO92/05757 A1 | 4/1992 |
| WO | WO96/06594 A1 | 3/1996 |
| WO | WO98/17238 A1 | 4/1998 |
| WO | WO00/67888 A1 | 11/2000 |
| WO | WO2005/063189 A1 | 7/2005 |
| WO | WO2009/083545 A2 | 7/2009 |

OTHER PUBLICATIONS

Engfeldt et al, DE 10361526, Machine Translation of Description, p. 1-4.*
PCT International Search Report (PCT/EP2009/067623) dated Apr. 20, 2011.

* cited by examiner

*Primary Examiner* — Blessing M Fubara
*Assistant Examiner* — Jennifer A Berrios
(74) *Attorney, Agent, or Firm* — David K. Benson

(57) ABSTRACT

The present invention relates to transparent antiperspirant compositions in the form of a water-in-oil emulsion, which contain a balanced mixture of selected oil components and emulsifiers in order to improve the antiperspirant effect.

10 Claims, No Drawings

TRANSPARENT ANTIPERSPIRANT GELS

CROSS-REFERENCES TO RELATED APPLICATIONS

This is a continuation of International Application No. PCT/EP2009/067623, filed Dec. 21, 2009, which claims priority to German Patent Application No. DE 10 2008 064 198.7 filed Dec. 22, 2008, both of which are hereby incorporated by reference.

FIELD OF THE INVENTION

The present invention generally relates to transparent perspiration-inhibiting compositions in the form of a water-in-oil emulsion that, in order to improve the perspiration-inhibiting effect, contain a balanced mixture of highly effective antiperspirant active substances, selected oil components and emulsifiers.

BACKGROUND OF THE INVENTION

Perspiration-inhibiting compositions in the form of a water-in-oil emulsion are already known in the existing art. WO 92/05767 A1 discloses transparent perspiration-inhibiting gels in the form of a water-in-oil emulsion based on cyclomethicones and emulsifying ethylene oxide/propylene oxide-substituted polydimethylsiloxanes. WO 96/06594 A1 discloses transparent perspiration-inhibiting water-in-oil compositions that contain volatile silicone oils and/or volatile hydrocarbon oils, and the silicone-free water-in-oil emulsifiers Laureth-1 or Laureth-4. WO 98/17238 A1 discloses perspiration-inhibiting sticks in the form of a water-in-oil emulsion based on silicone-free water-in-oil emulsifiers terminally disubstituted with alkyl residues, without addressing the problem of transparency. WO 00/67888 A1 discloses low-viscosity W/O emulsions having a viscosity of at most 5000 mPas, at least 75 wt % water phase, at most 20 wt % lipids, emulsifiers, and further lipophilic constituents, the oil phase having a total polarity between 20 and 30 mN/m and being free of silicones, stabilized by means of silicone-free water-in-oil emulsifiers terminally disubstituted with alkyl residues. This document also does not deal with the problem of transparency.

Transparent gels in the form of a water-in-oil emulsion are very popular among consumers. The known propellant gas-free W/O gels based on cyclomethicones produce a fresh and at the same time care-providing feel when applied onto the skin. At the same time, they initially exhibit no residues directly after application. This (at first) largely residue-free application, which is greatly appreciated by consumers, is also made visible to them by the transparency of the composition.

For optimum transparency, the refractive index of the oil phase and of the water phase must be matched to one another within approximately 0.001 or better, and preferably within approximately 0.0004. If a constituent resulting in a relatively high refractive index for the aqueous phase is stipulated, for example the particularly effective perspiration-inhibiting aluminum-zirconium compounds, this therefore limits the selection of the other constituents.

One problem with the known gels is their high cyclomethicone content. In the context of commercially usual cyclomethicones, a distinction is made principally among cyclotetrasiloxane, cyclopentasiloxane, and cyclohexasiloxane. Cyclotetrasiloxane, whose melting point of −11° C. is unusually high, can result in problems with shelf stability at the higher utilization quantities that are typical for a water-in-oil emulsion gel. In addition, the use of cyclotetrasiloxane is largely falling out of favor nowadays for toxicological reasons. The usual commercial cyclomethicone products are largely free of cyclotetrasiloxane. Even the trace concentration of cyclotetrasiloxane, however, means that the cyclomethicone substance class is a problematic raw material; cyclosiloxanes in general are furthermore being discussed because of their persistence in the environment. On the other hand, the cyclomethicones exhibit outstanding utilization properties, so that it is extremely difficult to replace them. Cyclomethicones are relatively volatile oil components. They are therefore popular for use in cosmetics, in particular in antiperspirants, because they help solve the problem of clothing stains. On the other hand, antiperspirants having too high a proportion of volatile cyclomethicones form white residues on the skin after drying, i.e. not until some time after application, which adhere poorly to the skin and can flake off; this is perceived by many consumers as unpleasant.

It would therefore be desirable to make available transparent perspiration-inhibiting compositions in the form of a water-in-oil emulsion that are largely or in fact entirely free of cyclomethicones. It would be further desirable to make available transparent perspiration-inhibiting compositions in the form of a water-in-oil emulsion that have a high concentration of dispersed aqueous phase, by preference at least 75 wt %. Because the commercially usual perspiration-inhibiting active substances are water-soluble, they are present in the aqueous phase. Rapid release of the active substance can be assisted by a high concentration of aqueous phase, and can be greatly improved by selecting the emulsifiers and additives in the aqueous phase.

Another desirable goal would be to make available transparent perspiration-inhibiting compositions in the form of a water-in-oil emulsion that have a gel-like consistency of medium to high viscosity, and can be applied by means of a roll-on applicator or a stick-like sleeve (cream dispenser). It would also be advantageous to make available transparent perspiration-inhibiting compositions in the form of a water-in-oil emulsion that are largely or in fact entirely free of cyclomethicones and exhibit good release of the perspiration-inhibiting active substance.

It would also be advantageous to make available transparent perspiration-inhibiting compositions in the form of a water-in-oil emulsion that are largely or in fact entirely free of cyclomethicones and have sufficient shelf stability. Another desirable goal would be to make available transparent perspiration-inhibiting compositions in the form of a water-in-oil emulsion that are largely or in fact entirely free of cyclomethicones and have sufficient shelf stability, and exhibit good release of the perspiration-inhibiting active substance.

Furthermore, other desirable features and characteristics of the present invention will become apparent from the subsequent detailed description of the invention and the appended claims, taken in conjunction with the accompanying drawings and this background of the invention.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has been found, surprisingly, that compositions in accordance with the following description of the invention achieve the above stated advantages and goals in outstanding fashion.

According to an exemplary embodiment of the invention, a transparent perspiration-inhibiting compositions in the form of a water-in-oil emulsion includes:
- 10 to 20 wt % external oil phase, containing
  - at least one symmetrical, asymmetrical, or cyclic ester of carbonic acid with linear or branched $C_6$ to $C_{22}$ alkanols,
  - at least one addition product of 1 to 14 propylene oxide units with mono- or polyvalent $C_{3-16}$ alkanols, and
  - cyclomethicone in a total quantity from 0 to at most 3 wt %,
- 75 to 90 wt % dispersed aqueous phase, therein at least one compound selected from water-soluble polyvalent $C_2$ to $C_9$ alkanols having 2 to 6 hydroxyl groups and from water-soluble polyethylene glycols having 3 to 20 ethylene oxide units, in a total quantity from 20 to 60 wt %, and 5 to 40 wt % (USP) of at least one perspiration-inhibiting aluminum-zirconium compound.
- at least one silicone-based water-in-oil emulsifier having at least one alkyl substituent R having 4 to 20 carbon atoms,
- no silicone-free water-in-oil emulsifier,
- free (=not molecularly bound) and molecularly bound water in a total quantity from 5 to 40 wt %, preferably 6 to 30 wt %, particularly preferably 7 to 22 wt %,
- at least 20 wt % of the at least one perspiration-inhibiting aluminum-zirconium compound, based on the total quantity of perspiration-inhibiting aluminum-zirconium compound, being solubilized in at least one compound selected from water-soluble polyvalent $C_2$ to $C_9$ alkanols having 2 to 6 hydroxyl groups and from water-soluble polyethylene glycols having 3 to 20 ethylene oxide units. All wt % indications in this context are based on the total weight of the emulsion.

Exemplary compositions according to the present invention contain 10 to 20 wt % external oil phase; the oil phase content is preferably 12 to 18 wt %, particularly preferably 14 to 16 wt %, based in each case on the total weight of the emulsion. In the present Application, the terms "external oil phase" and "oil phase" are used synonymously.

The silicone-based water-in-oil emulsifier, and if applicable further emulsifying constituents, are not considered to be oil phase for purposes of this Application. Lipophilic constituents that under standard conditions are not liquid ("oil") but instead are present in solid form, e.g. waxes, are considered to be oil phase for purposes of this Application. Perfume oils are considered to be oil phase for purposes of this Application. Ethanol that may optionally be contained, as well as the polyvalent $C_2$ to $C_9$ alkanols having 2 to 6 hydroxyl groups and the water-soluble polyethylene glycols having 3 to 20 ethylene oxide units, are considered for purposes of this Application to be not oil phase but water phase, even if they exhibit oil-soluble properties at least in part.

"Standard conditions" are, for purposes of this Application, a temperature of 20° C. and a pressure of 1013.25 mbar. Melting point indications likewise refer to a pressure of 1013.25 mbar.

The oil phase obligatorily contains a combination of at least one symmetrical, asymmetrical, or cyclic ester of carbonic acid with linear or branched $C_6$ to $C_{22}$ alkanols, and at least one addition product of 1 to 14 propylene oxide units with univalent or polyvalent $C_{3-16}$ alkanols.

It has been found, surprisingly, that this combination of oil components represents an outstanding replacement for the cyclomethicone component in known perspiration-inhibiting W/O emulsions. These oil combinations, surprisingly, assist active-substance release of the perspiration-inhibiting active substance. These oils furthermore offer a pleasant skin feel similar to that of cyclomethicone. Highly transparent W/O emulsions can furthermore be manufactured very effectively using these oils, because of their refractive indices.

Preferred oil components that represent symmetrical, asymmetrical, or cyclic esters of carbonic acid with linear or branched $C_6$ to $C_{22}$ alkanols are di-n-hexyl carbonate, di-n-heptyl carbonate, di-n-octyl carbonate, which is obtainable under the INCI name Dicaprylyl Carbonate, for example as the commercial product Cetiol® CC of Cognis, furthermore di-(-2-ethylhexyl) carbonate, which is obtainable under the INCI name Diethylhexyl Carbonate, for example as the commercial product Tegosoft® DEC of Degussa-Evonik, furthermore di-n-nonyl carbonate, di-n-decyl carbonate, di-n-lauryl carbonate, di-n-myristyl carbonate, di-($C_{14}$ to $C_{15}$) alkyl carbonate, di-n-cetyl carbonate, diisocetyl carbonate, di-n-stearyl carbonate, diisostearyl carbonate, diarachyl carbonate, and dibehenyl carbonate as symmetrically substituted carbonates, as well as asymmetrically substituted carbonates such as n-hexyl-n-octyl carbonate, n-hexyl-2-ethylhexyl carbonate, and n-octyl-n-decyl carbonate. Cyclic esters of carbonic acid are obtainable by transesterifying dimethyl carbonate or diethyl carbonate with divalent or polyvalent alkanols.

Particularly preferred compositions according to the present invention are characterized in that the at least one symmetrical, asymmetrical, or cyclic ester of carbonic acid with linear or branched $C_6$ to $C_{22}$ alkanols is selected from di-n-octyl carbonate, di-(2-ethylhexyl) carbonate, di-($C_{14}$ to $C_{15}$) alkyl carbonate, di-n-decyl carbonate, and di-n-lauryl carbonate.

Di-n-octyl carbonate, which has a refractive index nD (at 21° C.) of 1.435 to 1.436, as well as di-2-ethylhexyl carbonate, are extraordinarily preferred.

Preferred compositions according to the present invention are characterized in that at least one symmetrical, asymmetrical, or cyclic ester of carbonic acid with linear or branched $C_6$ to $C_{22}$ alkanols is contained in a total quantity from 8 to 18 wt %, particularly preferably 10 to 16 wt %, extraordinarily preferably 12 to 14 wt %, based on the entire composition.

Further particularly preferred compositions according to the present invention are characterized in that the hydrophobic oil phase without the emulsifiers is made up, at a proportion of at least 60 wt %, preferably at least 70 wt %, particularly at least 80 wt %, extraordinarily preferably at least 90 wt %, of at least one symmetrical, asymmetrical, or cyclic ester of carbonic acid with linear or branched $C_6$ to $C_{22}$ alkanols.

Further particularly preferred compositions according to the present invention are characterized in that the hydrophobic oil phase without the emulsifiers is made up, at a proportion of at least 60 wt %, preferably at least 70 wt %, particularly at least 80 wt %, extraordinarily preferably at least 90 wt %, of di-n-octyl carbonate.

Further particularly preferred compositions according to the present invention are characterized in that the hydrophobic oil phase without the emulsifiers is made up, at a proportion of at least 60 wt %, preferably at least 70 wt %, particularly at least 80 wt %, extraordinarily preferably at least 90 wt %, of di-2-ethylhexyl carbonate.

Further particularly preferred compositions according to the present invention are characterized in that the hydrophobic oil phase without the emulsifiers is made up, at a proportion of at least 60 wt %, preferably at least 70 wt %, particularly at least 80 wt %, extraordinarily preferably at least 90 wt %, of di-n-octyl carbonate and di-2-ethylhexyl carbonate.

As a further obligatory oil component, the compositions according to the present invention contain at least one addition product of 1 to 14 propylene oxide units with a mono- or polyvalent $C_{3-16}$ alcohol, in particular with n-butanol-1, n-pentanol-1, n-hexanol-1, n-heptanol-1, n-octanol-1, n-decanol-1, n-decane-1,10-diol, lauryl alcohol, myristyl alcohol, and cetyl alcohol. Addition products of 1 to 8 propylene oxide units with a mono- or polyvalent $C_{3-16}$ alcohol are preferred according to the present invention. Further preferred according to the present invention are addition products of 1 to 8 propylene oxide units with a monovalent $C_{3-16}$ alcohol. Further preferred according to the present invention are addition products of 2 to 3 propylene oxide units with a monovalent $C_{10-14}$ alkanol. Further preferred according to the present invention are addition products of 1 to 8 propylene oxide units with a monovalent $C_{3-16}$ alkanol, in particular with n-decanol-1, lauryl alcohol, and myristyl alcohol. Further preferred according to the present invention are addition products of 2 to 3 propylene oxide units with a monovalent $C_{10-14}$ alkanol, in particular with n-decanol-1, lauryl alcohol, and myristyl alcohol.

PPG-2 myristyl ether, PPG-3 myristyl ether (Witconol® APM), PPG-4 myristyl ether, PPG-5 myristyl ether, PPG-2 lauryl ether, PPG-3 lauryl ether, PPG-4 lauryl ether, PPG-5 lauryl ether, PPG-6 lauryl ether, PPG-2 decyl ether, PPG-3 decyl ether, PPG-4 decyl ether, PPG-5 decyl ether, PPG-6 decyl ether, PPG-7 decyl ether, PPG-2 octyl ether, PPG-3 octyl ether, PPG-4 octyl ether, PPG-5 octyl ether, PPG-6 octyl ether, PPG-7 octyl ether, PPG-8 octyl ether, PPG-2 hexyl ether, PPG-3 hexyl ether, PPG-4 hexyl ether, PPG-5 hexyl ether, PPG-6 hexyl ether, PPG-7 hexyl ether, PPG-8 hexyl ether, and PPG-9 hexyl ether are particularly preferred.

Also suitable, although less preferred, are PPG-4 butyl ether, PPG-5 butyl ether, PPG-6 butyl ether, PPG-7 butyl ether, PPG-8 butyl ether, PPG-9 butyl ether, PPG-10 butyl ether, PPG-11 butyl ether, PPG-12 butyl ether, PPG-13 butyl ether, and PPG-14 butyl ether (Ucon® Fluid AP).

It has been found, surprisingly, that with a PPG addition product such as PPG-15 stearyl ether (Arlamol® E), it was not possible to achieve the same good effects with regard to release of the perspiration-inhibiting active substance as with the addition products of 1 to 14 propylene oxide units with mono- or polyvalent $C_{3-16}$ alkanols. PPG-3 myristyl ether and PPG-2 myristyl ether are particularly preferred according to the present invention; PPG-3 myristyl ether is extraordinarily preferred. Combinations of di-n-octyl carbonate and PPG-3 myristyl ether, di-2-ethylhexyl carbonate and PPG-3 myristyl ether, di-n-octyl carbonate and PPG-2 myristyl ether, and di-2-ethylhexyl carbonate and PPG-2 myristyl ether are extraordinarily preferred according to the present invention.

The at least one addition product of 1 to 14, preferably 1 to 8 propylene oxide units with a mono- or polyvalent $C_{3-16}$ alkanol, preferably with a monovalent C10-14 alkanol, is contained in a total quantity preferably from 0.8 to 4 wt %, preferably 1 to 3 wt %, particularly preferably 2 to 2.5 wt %, based in each case on the entire preparation.

Further perspiration-inhibiting compositions preferred according to the present invention are characterized in that PPG-3 myristyl ether is contained in a quantity from 0.8 to 4 wt %, preferably 1 to 3 wt %, particularly preferably 2 to 2.5 wt %, based in each case on the entire composition. Further perspiration-inhibiting compositions preferred according to the present invention are characterized in that PPG-2 myristyl ether is contained in a quantity from 0.8 to 4 wt %, preferably 1 to 3 wt %, particularly preferably 2 to 2.5 wt %, based in each case on the entire composition.

Compositions particularly preferred according to the present invention are characterized in that the oil components that represent symmetrical, asymmetrical, or cyclic esters of carbonic acid with linear or branched $C_6$ to $C_{22}$ alkanols are present at a weight ratio from 4 to 19 with respect to the oil components that represent addition products of 1 to 14 propylene oxide units with mono- or polyvalent $C_{3-16}$ alkanols. This weight ratio is preferably 5 to 15, particularly preferably 6 to 14, and extraordinarily preferably 7 to 13. It has been found that particularly good effects with regard to release of the perspiration-inhibiting active substance can be achieved with a preferred weight ratio.

The compositions according to the present invention are characterized in that 0 to a maximum of 3 wt %, preferably 0 to a maximum of 2.5 wt %, particularly preferably 0 to a maximum of 2 wt %, extraordinarily preferably 0 to a maximum of 1 wt % cyclomethicone is contained, based in each case on the total weight of the emulsion.

Preferred compositions according to the present invention are further characterized in that linear polymethylsiloxanes or polydimethylsiloxanes having a kinematic viscosity at 25° C. of 20 cSt and below are contained in a total quantity from 0 to a maximum of 3 wt %, preferably 0 to a maximum of 2.5 wt %, particularly preferably 0 to a maximum of 2 wt %, extraordinarily preferably 0 to a maximum of 1 wt %.

The compositions according to the present invention furthermore contain 75 to 90 wt % dispersed aqueous phase having at least one perspiration-inhibiting active substance and having at least one compound selected from water-soluble polyvalent $C_2$ to $C_9$ alkanols having 2 to 6 hydroxyl groups and from water-soluble polyethylene glycols having 3 to 20 ethylene oxide units.

The concentration of aqueous phase is preferably 78 to 88 wt %, particularly preferably 80 to 86 wt %, and extraordinarily preferably 81 to 84 wt %, based in each case on the total weight of the emulsion.

The total concentration of free water (=not molecularly bound) and molecularly bound water is 5 to 40 wt %, preferably 6 to 30 wt %, particularly preferably 7 to 22 wt %, based in each case on the total weight of the emulsion. A total water content of 16, 17, 18, 19, 20, and 21 wt %, based in each case on the entire composition according to the present invention, can be extraordinarily preferred.

"Molecularly bound" water is understood for purposes of the present Application as, in particular, water of crystallization, for example from the perspiration-inhibiting active substances. "Free" water is water that is added as such in the context of emulsion manufacturing, or is introduced via the raw materials as non-molecularly-bound water.

Further preferred compositions according to the present invention are characterized in that 1 to 10 wt %, preferably 2 to 8 wt %, particularly preferably 3 to 7 wt %, extraordinarily preferably 4 to 6 wt % ethanol is contained, based in each case on the total weight of the emulsion. An ethanol content of this kind advantageously assists emulsion stability and transparency. Other compositions according to the present invention that are likewise preferred are characterized in that they contain no ethanol.

Emulsifying constituents are not considered to be aqueous phase for purposes of this Application.

Aluminum-Zirconium Compounds

The compositions according to the present invention contain 5 to 40 wt %, preferably 10 to 35 wt %, particularly preferably 11 to 28 wt %, and extraordinarily preferably 12 to 20 wt %, based in each case on the total weight of the ligand-free, water-free, and water of crystallization-free active substance (USP) in the overall composition, of at least one perspiration-inhibiting aluminum-zirconium compound, at least 20 wt % of the at least one perspiration-inhibiting aluminum-zirconium compound, based on the total weight of perspiration-inhibiting aluminum-zirconium compound, being solubilized in at least one compound selected from water-soluble polyvalent $C_2$ to $C_9$ alkanols having 2 to 6 hydroxyl groups and from water-soluble polyethylene glycols having 3 to 20 ethylene oxide units.

Further compositions that are likewise preferred according to the present invention are characterized in that the at least one antiperspirant active substance is contained in a quantity from 5 to 40 wt %, preferably 8 to 25 wt %, preferably 10 to 22, and particularly preferably 13 to 20 wt %, based on each case on the total weight of the ligand-free, water-free, and water of crystallization-free active substance (USP) in the overall composition.

"Water solubility" is understood according to the present invention as a solubility of at least 5 wt % at 20° C. under standard conditions, i.e. that quantities of at least 5 g of the polyvalent $C_2$ to $C_9$ alkanol having 2 to 6 hydroxyl groups, or of the polyethylene glycol having 3 to 20 ethylene oxide units, are soluble in 95 g water at 20° C.

Aluminum-zirconium glycol complexes are preferred according to the present invention, aluminum-zirconium propylene glycol complexes being particularly preferred. Aluminum-zirconium glycol complexes that are the subject matter of U.S. Pat. No. 5,643,558 and U.S. Pat. No. 6,010,688 are furthermore particularly preferred. Particularly preferred perspiration-inhibiting active substances are also complexes of activated perspiration-inhibiting aluminum-zirconium compounds with a polyvalent alcohol that contain 20 to 50 wt %, particularly preferably 20 to 42 wt %, activated perspiration-inhibiting aluminum-zirconium compound and 2 to 16 wt % molecularly bound water, the remainder to make 100% being at least one polyol having 3 to 6 carbon atoms and 3 to 6 hydroxyl groups. Propylene glycol, propylene glycol/sorbitol mixtures, and propylene glycol/pentaerythritol mixtures are preferred polyols of this kind.

Complexes of this kind, of an activated perspiration-inhibiting aluminum-zirconium compound with a polyol, that are preferred according to the present invention are disclosed, for example, in U.S. Pat. No. 5,643,558 and U.S. Pat. No. 6,245,325.

Further preferred perspiration-inhibiting active substances are aluminum-zirconium chlorohydrates, such as aluminum-zirconium trichlorohydrate, aluminum-zirconium tetrachlorohydrate, aluminum-zirconium pentachlorohydrate, aluminum-zirconium octachlorohydrate, aluminum-zirconium chlorohydrate glycine complexes such as aluminum-zirconium trichlorohydrex glycine, aluminum-zirconium tetrachlorohydrex glycine, aluminum-zirconium pentachlorohydrex glycine, and aluminum-zirconium octachlorohydrex glycine.

Also particularly preferred according to the present invention are perspiration-inhibiting compositions in which 20 to 100 wt % of the at least one perspiration-inhibiting aluminum-zirconium compound is made up of at least one complex of a perspiration-inhibiting aluminum-zirconium compound with a polyvalent alcohol that contains 20 to 50 wt %, particularly preferably 20 to 42 wt % perspiration-inhibiting aluminum-zirconium compound and 2 to 16 wt % molecularly bound water, the remainder to make 100% being at least one compound selected from water-soluble polyvalent $C_2$ to $C_9$ alkanols having 2 to 6 hydroxyl groups and from water-soluble polyethylene glycols having 3 to 20 ethylene oxide units.

Antiperspirant active substances particularly preferred according to the present invention are selected from so-called "activated" aluminum-zirconium compounds, which are also referred to as "enhanced activity" antiperspirant active substances. Such active substances are known in the existing art and are also commercially obtainable. The manufacture thereof is disclosed, for example, in GB 2 048 229, U.S. Pat. No. 4,775,528, and U.S. Pat. No. 6,010,688. Activated aluminum-zirconium compounds are, as a rule, produced by heat treatment of a relatively dilute solution of the salt (e.g. approx. 10 wt % salt) in order to increase its HPLC peak-4 to peak-3 area ratio. The activated salt can then be dried to a powder, in particular spray-dried. In addition to spray drying, drum drying is also, for example, suitable.

Activated aluminum-zirconium compounds typically have an HPLC peak-4 to peak-3 area ratio of at least 0.4, preferably at least 0.7, particularly preferably at least 0.9, at least 70 wt % of the aluminum being attributable to these peaks.

Both activated and non-activated aluminum-zirconium compounds can be used as a dried, e.g. spray-dried, powder. In a particularly preferred embodiment, this powder is used as a solubilizate in at least one polyol, selected from water-soluble polyvalent $C_2$ to $C_9$ alkanols having 2 to 6 hydroxyl groups and from water-soluble polyethylene glycols having 3 to 20 ethylene oxide units. These water-soluble polyol components are preferably selected from 1,2-propylene glycol, 1,3-propylene glycol, 2-methyl-1,3-propanediol, glycerol, butylene glycols such as preferably 1,2-butylene glycol, particularly preferably 1,3-butylene glycol, and 1,4-butylene glycol, pentaerythritol, pentylene glycols such as 1,2-pentanediol and 1,5-pentanediol, hexanediols such as, particularly preferably, 1,2-hexanediol and 1,6-hexanediol, hexanetriols such 1,2,6-hexanetriol, 1,2-octanediol, 1,8-octanediol, dipropylene glycol, tripropylene glycol, diglycerol, triglycerol, and mixtures of the aforesaid substances. Preferred water-soluble polyethylene glycols are selected from PEG-3, PEG-4, PEG-6, PEG-7, PEG-8, PEG-9, PEG-10, PEG-12, PEG-14, PEG-16, PEG-18, and PEG-20 as well as mixtures thereof, PEG-3 to PEG-8 being particularly preferred. Preferred solubilizing agents are 1,2-propylene glycol, 1,3-butylene glycol, dipropylene glycol, and 1,2-hexanediol as well as mixtures thereof. Preferred solubilizing polyol mixtures contain 1,2-propylene glycol and dipropylene glycol. Particularly preferred polyol mixtures contain 1,2-propylene glycol and dipropylene glycol at a weight ratio from 4:1 to 2:1.

Perspiration-inhibiting active substances that are likewise preferred according to the present invention are nonaqueous solutions or solubilizates of an activated perspiration-inhibiting aluminum-zirconium compound, for example in accordance with U.S. Pat. No. 6,010,688, that are stabilized against loss of activation, with respect to a rapid decrease in the HPLC peak-4 to peak-3 area ratio of the compound, by the addition of an effective quantity of a polyvalent alcohol that comprises 3 to 6 carbon atoms and 3 to 6 hydroxyl groups, preferably propylene glycol, sorbitol, and pentaerythritol. Preferred, for example, are antiperspirant active-substance solutions or solubilizates (which does not mean the emulsions according to the present invention) that contain, in weight percent (USP): 18 to 45 wt % of an activated aluminum-zirconium salt, 55 to 82 wt % of at least one anhydrous polyvalent alcohol having 3 to 6 carbon atoms and 3 to 6 hydroxyl groups, preferably propylene glycol, butylene glycol, diethylene glycol, dipropylene glycol, glycerol, sorbitol, and pentaerythritol, particularly preferably propylene glycol.

Also particularly preferred are complexes of activated perspiration-inhibiting aluminum-zirconium salts with a polyvalent alcohol that contain 20 to 50 wt %, particularly preferably 20 to 42 wt %, activated perspiration-inhibiting aluminum-zirconium salt, and 2 to 16 wt % molecularly bound water, the remainder to make 100 wt % being at least one polyvalent alcohol having 3 to 6 carbon atoms and 3 to 6 hydroxyl groups. Propylene glycol, propylene glycol/sorbitol mixtures, and propylene glycol/pentaerythritol mixtures are preferred alcohols of this kind. Complexes of this kind preferred according to the present invention, of an activated perspiration-inhibiting aluminum-zirconium salt with a polyvalent alcohol, are disclosed, for example, in U.S. Pat. No. 5,643,558 and U.S. Pat. No. 6,245,325.

Further preferred perspiration-inhibiting active substances are calcium-aluminum salts such as those disclosed, for example, in U.S. Pat. No. 2,571,030. These salts are manufactured by reacting calcium carbonate with aluminum chlorohydroxide or aluminum chloride and aluminum powder, or by adding calcium chloride dihydrate to aluminum chlorohydroxide.

Further preferred perspiration-inhibiting active substances are aluminum-zirconium complexes such as those disclosed, for example, in U.S. Pat. No. 4,017,599, which are buffered with salts of amino acids, in particular with alkali glycinates and alkaline-earth glycinates.

Further preferred perspiration-inhibiting active substances are activated aluminum-zirconium salts such as those disclosed, for example, in U.S. Pat. No. 6,245,325 or U.S. Pat. No. 6,024,816, containing 5 to 78 wt % (USP) of an activated perspiration-inhibiting aluminum-zirconium salt, an amino acid or hydroxyalkanoic acid in a quantity such as to make available a weight ratio of (amino acid or hydroxyalkanoic acid) to (Al+Zr) from 2:1 to 1:20 and preferably 1:1 to 1:10, as well as a water-soluble calcium salt in a quantity such as to make available a Ca:(Al+Zr) weight ratio from 1:1 to 1:28 and preferably 1:2 to 1:25.

Particularly preferred solid activated perspiration-inhibiting salt compositions, for example according to U.S. Pat. No. 6,245,325 or U.S. Pat. No. 6,042,816, contain 48 to 78 wt % (USP), preferably 66 to 75 wt %, of an activated aluminum-zirconium salt and 1 to 16 wt %, preferably 4 to 13 wt % molecularly bound water (water of hydration), as well as sufficient water-soluble calcium salt that the Ca:(Al+Zr) weight ratio is equal to 1:1 to 1:28, preferably 1:2 to 1:25, and sufficient amino acid that the weight ratio of amino acid to (Al+Zr) is equal to 2:1 to 1:20, preferably 1:1 to 1:10.

Further particularly preferred solid activated perspiration-inhibiting salt compositions, for example according to U.S. Pat. No. 6,245,325 or U.S. Pat. No. 6,042,816, contain 48 to 78 wt % (USP), preferably 66 to 75 wt %, of an activated aluminum-zirconium salt and 1 to 16 wt %, preferably 4 to 13 wt % molecularly bound water (water of hydration), as well as sufficient water-soluble calcium salt that the Ca:(Al+Zr) weight ratio is equal to 1:1 to 1:28, preferably 1:2 to 1:25, and sufficient glycine that the weight ratio of glycine to (Al+Zr) is equal to 2:1 to 1:20, preferably 1:1 to 1:10.

Further particularly preferred solid activated perspiration-inhibiting salt compositions, for example according to U.S. Pat. No. 6,245,325 or U.S. Pat. No. 6,042,816, contain 48 to 78 wt % (USP), preferably 66 to 75 wt % of an activated aluminum-zirconium salt and 1 to 16 wt %, preferably 4 to 13 wt % molecularly bound water, as well as sufficient water-soluble calcium salt that the Ca:(Al+Zr) weight ratio is equal to 1:1 to 1:28, preferably 1:2 to 1:25, and sufficient hydroxyalkanoic acid that the weight ratio of hydroxyalkanoic acid to (Al+Zr) is equal to 2:1 to 1:20, preferably 1:1 to 1:10.

Water-soluble calcium salts preferred for stabilization of the perspiration-inhibiting salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

Amino acids preferred for stabilization of the perspiration-inhibiting salts are selected from glycine, alanine, leucine, isoleucine, β-alanine, valine, cysteine, serine, tryptophan, phenylalanine, methionine, β-amino-n-butanoic acid, and γ-amino-n-butanoic acid, and salts thereof, respectively in the d-form, l-form, and dl-form; glycine is particularly preferred.

Hydroxyalkanoic acids preferred for stabilization of the perspiration-inhibiting salts are selected from glycolic acid and lactic acid.

Further preferred perspiration-inhibiting active substances are activated aluminum-zirconium salts, for example such as those disclosed in U.S. Pat. No. 6,902,723, containing 5 to 78 wt % (USP) of an activated perspiration-inhibiting aluminum-zirconium salt, an amino acid or hydroxyalkanoic acid in a quantity such as to make available an (amino acid or hydroxyalkanoic acid) to (Al+Zr) weight ratio from 2:1 to 1:20 and preferably 1:1 to 1:10, and a water-soluble strontium salt in a quantity such as to make available a Sr:(Al+Zr) weight ratio from 1:1 to 1:28, and preferably 1:2 to 1:25.

Particularly preferred solid activated perspiration-inhibiting salt compositions, for example according to U.S. Pat. No. 6,902,723, contain 48 to 78 wt % (USP), preferably 66 to 75 wt % of an activated aluminum-zirconium salt and 1 to 16 wt %, preferably 4 to 13 wt % molecularly bound water, as well as sufficient water-soluble strontium salt that the Sr:(Al+Zr) weight ratio is equal to 1:1 to 1:28, preferably 1:2 to 1:25, and sufficient amino acid that the weight ratio of amino acid to (Al+Zr) is equal to 2:1 to 1:20, preferably 1:1 to 1:10.

Further particularly preferred solid activated perspiration-inhibiting salt compositions, for example according to U.S. Pat. No. 6,902,723, contain 48 to 78 wt % (USP), preferably 66 to 75 wt % of an activated aluminum-zirconium salt and 1 to 16 wt %, preferably 4 to 13 wt % molecularly bound water, as well as sufficient water-soluble strontium salt that the Sr:(Al+Zr) weight ratio is equal to 1:1 to 1:28, preferably 1:2 to 1:25, and sufficient glycine that the weight ratio of glycine to (Al+Zr) is equal to 2:1 to 1:20, preferably 1:1 to 1:10.

Further particularly preferred solid activated perspiration-inhibiting salt compositions, for example according to U.S. Pat. No. 6,902,723, contain 48 to 78 wt % (USP), preferably 66 to 75 wt % of an activated aluminum-zirconium salt and 1 to 16 wt %, preferably 4 to 13 wt % molecularly bound water, as well as sufficient water-soluble strontium salt that the Sr:(Al+Zr) weight ratio is equal to 1:1 to 1:28, preferably 1:2 to 1:25, and sufficient hydroxyalkanoic acid that the weight ratio of hydroxyalkanoic acid to (Al+Zr) is equal to 2:1 to 1:20, preferably 1:1 to 1:10.

Preferred activated aluminum-zirconium salts are those that represent mixtures or complexes of the aluminum salts described above with zirconium salts of the $ZrO(OH)_{2-pb}Y_b$, in which Y is Cl, Br, I, $NO_3$ or $SO_4$, b is a rational number from 0.8 to 2, and p is the valence of Y, such as those disclosed e.g. in U.S. Pat. No. 6,074,632. The zirconium salts as a rule also have some associatively bound water of hydration, typically 1 to 7 mol water per mol salt. The zirconium salt is by preference zirconyl hydroxychloride having the formula $ZrO(OH)_{2-b}Cl_b$, in which b is a rational number from 0.8 to 2, preferably 1.0 to 1.9. Preferred aluminum-zirconium salts have a molar Al:Zr ratio from 2 to 10, and a metal:(X+Y) ratio from 0.73 to 2.1, preferably 0.9 to 1.5. A particularly preferred salt is aluminum-zirconium chlorohydrate (i.e. X and Y are Cl) that has a molar Al:Zr ratio from 2 to 10 and a molar metal:Cl ratio from 0.9 to 2.1. The term "aluminum-zirconium chlorohydrate" encompasses the tri-, tetra-, penta-, and octachlorohydrate forms.

Zirconium salts preferred according to the present invention have the general formula $ZrO(OH)_{2-a}Cl_a \cdot x\ H_2O$ where $a=1.5$ to $1.87$ and $x=1$ to $7$, and $a$ and $x$ are rational numbers. These zirconium salts are disclosed, for example, in the Belgian document BE 825146.

Further preferred perspiration-inhibiting active substances are disclosed in U.S. Pat. No. 6,663,854 and US 2004 0009133.

The perspiration-inhibiting active substances can be present both in solubilized and in undissolved suspended form.

Preferred activated aluminum-zirconium salts have a molar metal-to-chloride ratio from 0.9 to 2.0, preferably 1.0 to 1.51, particularly preferably 1.1 to 1.5, extraordinarily preferably 1.3 to 1.4. Preferred aluminum-zirconium chlorohydrates have the empirical formula $Al_nZr(OH)_{[3n+4-m(n+1)]}(Cl)_{[m(n+1)]}$, where $n=2.0$ to $10.0$, preferably $3.0$ to $8.0$, $m=0.77$ to $1.11$ (corresponding to a molar ratio of metal (Al+Zr) to chloride from 1.3 to 0.9), preferably $m=0.91$ to $1.11$ (corresponding to M:Cl=1.1 to 0.9), and particularly preferably $m=1.00$ to $1.11$ (corresponding to M:Cl=1.0 to 0.9), also very preferably $m=1.02$ to $1.11$ (corresponding to M:Cl=0.98 to 0.9) and very preferably $m=1.04$ to $1.11$ (corresponding to M:Cl=0.96 to 0.9).

Further preferred aluminum-zirconium trichlorohydrates have the empirical formula $Al_4(OH)_{10}Cl_2 \cdot Zr(OH)Cl$. Further preferred aluminum-zirconium tetrachlorohydrates have the empirical formula $Al_4(OH)_{10}Cl_2 \cdot ZrCl_2$. Further preferred aluminum-zirconium pentachlorohydrates have the empirical formula $Al_8(OH)_{20}Cl_6 \cdot Zr(OH)Cl$. Further preferred aluminum-zirconium octachlorohydrates have the empirical formula $Al_8(OH)_{18}Cl_6 \cdot Zr(OH)Cl$. In these salts, some water of hydration is generally associatively bound, typically 1 to 6 mol water per mol of salt, corresponding to 1 to 16 wt %, preferably 4 to 13 wt % water of hydration.

Preferred perspiration-inhibiting salts are aluminum-zirconium tetrachlorohydrates (molar ratio Al:Zr=2 to 6; M:Cl=0.9 to 1.3), in particular salts having a molar ratio of metal to chloride from 0.9 to 1.1, in particular 0.9 to 1.0.

The preferred aluminum-zirconium chlorohydrates are usually associated with an amino acid in order to prevent polymerization of the zirconium species during manufacture. Preferred stabilizing amino acids are selected from glycine, alanine, leucine, isoleucine, β-alanine, cysteine, valine, serine, tryptophan, phenylalanine, methionine, β-amino-n-butanoic acid, and γ-amino-n-butanoic acid, and salts thereof, respectively in the d-form, l-form, and dl-form; glycine is particularly preferred. The amino acid is contained in the salt in a quantity from 1 to 3 mol, preferably 1.3 to 1.8 mol, in each case per mol of zirconium.

The aforementioned aluminum-zirconium trichlorohydrates, aluminum-zirconium tetrachlorohydrates, aluminum-zirconium pentachlorohydrates, and aluminum-zirconium octachlorohydrates, both activated and non-activated, are preferably present as a complex with glycine.

Particularly preferred perspiration-inhibiting active substances are selected from activated aluminum-zirconium trichlorohydrex glycines, in particular activated aluminum-zirconium trichlorohydrex glycines having a water of crystallization-free and glycine-free active substance (USP) from 69.5 to 88 wt %, preferably 72 to 85 wt %, particularly preferably 77 to 80 wt %, based in each case on the raw material as is, having a molar metal:Cl ratio from 0.9 to 1.5, and having a molar Al:Zr ratio from 3.4 to 3.8.

Further particularly preferred perspiration-inhibiting active substances are selected from non-activated aluminum-zirconium trichlorohydrex glycines, in particular non-activated aluminum-zirconium trichlorohydrex glycines having a water of crystallization-free and glycine-free active substance (USP) from 69.5 to 88 wt %, preferably 72 to 85 wt %, particularly preferably 77 to 80 wt %, based in each case on the raw material as is, having a molar metal:Cl ratio from 0.9 to 1.5, and having a molar Al:Zr ratio from 3.4 to 3.8.

Further particularly preferred perspiration-inhibiting active substances are selected from activated aluminum-zirconium tetrachlorohydrex glycines, in particular activated aluminum-zirconium tetrachlorohydrex glycines having a water of crystallization-free and glycine-free active substance (USP) from 72 to 88 wt %, preferably 77 to 85 wt %, based in each case on the raw material as is, having a molar metal:Cl ratio from 0.9 to 1.5, and having a molar Al:Zr ratio from 3.4 to 3.8.

Further particularly preferred perspiration-inhibiting active substances are selected from non-activated aluminum-zirconium tetrachlorohydrex glycines, in particular non-activated aluminum-zirconium tetrachlorohydrex glycines having a water of crystallization-free and glycine-free active substance (USP) from 72 to 88 wt %, preferably 77 to 85 wt %, based in each case on the raw material as is, having a molar metal:Cl ratio from 0.9 to 1.5, and having a molar Al:Zr ratio from 3.4 to 3.8. Further particularly preferred perspiration-inhibiting active substances are selected from activated aluminum-zirconium pentachlorohydrex glycines, in particular activated aluminum-zirconium pentachlorohydrex glycines having a water of crystallization-free and glycine-free active substance (USP) from 72 to 88 wt %, preferably 77 to 86 wt %, particularly preferably 78 to 81.5 wt %, based in each case on the raw material as is, having a molar metal:Cl ratio from 1.51 to 2.0, and having a molar Al:Zr ratio from 9.2 to 9.8. Further particularly preferred perspiration-inhibiting active substances are selected from non-activated aluminum-zirconium pentachlorohydrex glycines, in particular non-activated aluminum-zirconium pentachlorohydrex glycines having a water of crystallization-free and glycine-free active substance (USP) from 72 to 88 wt %, preferably 77 to 86 wt %, particularly preferably 78 to 81.5 wt %, based in each case on the raw material as is, having a molar metal:Cl ratio from 1.51 to 2.0, and having a molar Al:Zr ratio from 9.2 to 9.8.

In the case of the aforesaid aluminum-zirconium trichlorohydrex glycines, aluminum-zirconium tetrachlorohydrex glycines, aluminum-zirconium pentachlorohydrex glycines, and aluminum-zirconium octachlorohydrex glycines, both activated and non-activated, the water of crystallization content is 1.5 to 20 wt %, preferably 7 to 15 wt %, based in each case on the raw material as is.

Further preferred aluminum-zirconium trichlorohydrex glycines have the empirical formula $[Al_4(OH)_{10}Cl_2 \cdot Zr(OH)Cl] \cdot NH_2CH_2COOH$. Further preferred aluminum-zirconium tetrachlorohydrex glycines have the empirical formula $[Al_4(OH)_{10}Cl_2 \cdot ZrOCl_2] \cdot NH_2CH_2COOH$. Further preferred aluminum-zirconium pentachlorohydrex glycines have the empirical formula $[Al_8(OH)_{20}Cl_4 \cdot Zr(OH)Cl] \cdot NH_2CH_2COOH$. Further preferred aluminum-zirconium octachlorohydrex glycines have the empirical formula $[Al_8(OH)_{18}Cl_6 \cdot Zr(OH)Cl] \cdot NH_2CH_2COOH$ or $[Al_8(OH)_{18}Cl_6 \cdot ZrOCl_2] \cdot NH_2CH_2COOH$.

Also preferred according to the present invention are aluminum-zirconium chlorohydrate glycine salts that are stabilized with betaine $((CH_3)_3N^+-CH_2-COO^-)$. Particularly preferred corresponding compounds have a molar ratio of total (betaine+glycine) to Zr from (0.1 to 3.0):1, preferably (0.7 to 1.5):1, and a molar ratio of betaine to glycine of at least 0.001:1. Corresponding compounds are disclosed, for example, in U.S. Pat. No. 7,105,691.

In a particularly preferred embodiment according to the present invention, a so-called "activated" salt is contained as a particularly effective antiperspirant salt, in particular one having a high HPLC peak-5 aluminum content, in particular having a peak-5 area of at least 33%, particularly preferably at least 45%, based on the total area under peaks 2 to 5, measured by HPLC in a 10 wt % aqueous solution of the active substance under conditions in which the aluminum species are resolved into at least four successive peaks (referred to as peaks 2 to 5). Preferred aluminum-zirconium salts having a high HPLC peak-5 aluminum content (also called "E$^5$AZCH") are disclosed, for example, in U.S. Pat. No. 6,436,381 and U.S. Pat. No. 6,649,152.

Also preferred are those activated "E$^5$AZCH" salts whose HPLC peak-4 to peak-3 area ratio is equal to at least 0.4, preferably at least 0.7, particularly preferably at least 0.9. Further particularly preferred antiperspirant active substances are those aluminum-zirconium salts having a high HPLC peak-5 aluminum content that are additionally stabilized with a water-soluble strontium salt and/or with a water-soluble calcium salt. Corresponding salts are disclosed, for example, in U.S. Pat. No. 6,923,952.

Further preferred antiperspirant active substances are selected from astringent titanium salts, such as those disclosed e.g. in GB 2 299 506 A.

The antiperspirant active substances can be used as non-aqueous solutions or as glycolic solubilizates.

Aluminum-zirconium tetrachlorohydrex glycine complexes that are solubilized in at least one compound selected from water-soluble polyvalent $C_2$ to $C_9$ alkanols having 2 to 6 hydroxyl groups and from water-soluble polyethylene glycols having 3 to 20 ethylene oxide units, are particularly preferred.

Aluminum-zirconium tetrachlorohydrex glycine complexes are marketed as a powder, for example by Summit Reheis under the designation Rezal® 36 GP or, in activated form, as Summit Reach® AZP-908, Summit AZG-369, or Summit AZG-364.

Also particularly preferred are aluminum-zirconium pentachlorohydrex glycine complexes that are solubilized in at least one compound selected from water-soluble polyvalent $C_2$ to $C_9$ alkanols having 2 to 6 hydroxyl groups and from water-soluble polyethylene glycols having 3 to 20 ethylene oxide units. Such aluminum-zirconium pentachlorohydrex glycine complexes are marketed as a powder, for example by Summit, in activated form, under the designation AAZG-3110.

The aqueous or hydrophilic phase of the compositions according to the present invention furthermore encompasses at least one compound selected from water-soluble polyvalent $C_2$ to $C_9$ alkanols having 2 to 6 hydroxyl groups and from water-soluble polyethylene glycols having 3 to 20 ethylene oxide units. The addition of these compounds is necessary in particular in order to produce the transparency of the entire emulsion. Without these polyols, the refractive index of the aqueous or hydrophilic phase would be too low to be capable of being equalized with the refractive index of the oil phase. These water-soluble polyol components moreover contribute to the stability of the emulsion.

These water-soluble polyol components are preferably selected from 1,2-propylene glycol, 1,3-propylene glycol, 2-methyl-1,3-propanediol, glycerol, butylene glycols such as preferably 1,2-butylene glycol, particularly preferably 1,3-butylene glycol, and 1,4-butylene glycol, pentylene glycols such as 1,2-pentanediol and 1,5-pentanediol, hexanediols such as, particularly preferably, 1,2-hexanediol and 1,6-hexanediol, hexanetriols such as 1,2,6-hexanetriol, 1,2-octanediol, 1,8-octanediol, dipropylene glycol, tripropylene glycol, diglycerol, triglycerol, and mixtures of the aforesaid substances. Preferred water-soluble polyethylene glycols are selected from PEG-3, PEG-4, PEG-6, PEG-7, PEG-8, PEG-9, PEG-10, PEG-12, PEG-14, PEG-16, PEG-18, and PEG-20, as well as mixtures thereof, PEG-3 to PEG-8 being particularly preferred. Sugars, sugar alcohols, and certain sugar derivatives such as pentaerythritol, erythritol, sorbitol, xylitol, fructose, glucose, maltose, maltitol, mannitol, inositol, sucrose, trehalose, and xylose can also be used according to the present invention, but because of their tackiness are less suitable or are suitable only in small quantities.

1,2-Propylene glycol, 1,3-butylene glycol, dipropylene glycol, and 1,2-hexanediol, as well as mixtures thereof, are preferred. Preferred polyol mixtures contain 1,2-propylene glycol and dipropylene glycol. Particularly preferred polyol mixtures contain 1,2-propylene glycol and dipropylene glycol at a weight ratio from 4:1 to 2:1. These mixtures exhibit particularly balanced properties with regard to transparency, active-substance release, skin feel, and skin compatibility.

Preferred compositions according to the present invention are characterized in that the at least one compound selected from water-soluble polyvalent $C_2$ to $C_9$ alkanols having 2 to 6 hydroxyl groups and from water-soluble polyethylene glycols having 3 to 20 ethylene oxide units is contained in a total quantity from 20 to 60 wt %, preferably 25 to 55 wt %, particularly preferably 30 to 50 wt %, extraordinarily preferably 35 to 45 wt %, based in each case on the total weight of the emulsion.

The compositions according to the present invention furthermore encompass at least one silicone-based water-in-oil emulsifier having at least one alkyl substituent R having 4 to 20 carbon atoms.

It has been found, surprisingly, that water-in-oil emulsifiers that are silicone-based make possible better product performance in terms of faster release of the perspiration-inhibiting active substance. In comparison therewith, water-in-oil emulsions that exhibited all the features claimed in accordance with the present invention except for the silicone-based water-in-oil emulsifier, but were stabilized with PEG-30 Dipolyhydroxystearate (a typical silicone-free water-in-oil emulsifier) instead of with a silicone-based water-in-oil emulsifier, were considerably poorer in terms of fast release of the perspiration-inhibiting active substance.

In a preferred embodiment, the perspiration-inhibiting compositions according to the present invention are free of PEG-30 Dipolyhydroxystearate.

In addition, the silicone-free water-in-oil emulsifiers Isolan GPS (Evonik), a mixture of Polyglyceryl-4 Diisostearate, Polyhydroxystearate, and Polyhydroxysebacate, and also Laureth-2, PEG-6 Caprylic/Capric Glycerides, PPG-15 Stearyl Ether, and PEG-7 Glyceryl Cocoate, were tested: Laureth-2 and PEG-7 Glyceryl Cocoate did not yield stable emulsions, and the other silicone-free water-in-oil emulsifiers did not produce improved active-substance release.

A group of water-in-oil emulsifiers that is particularly preferred according to the present invention is the poly-($C_2$ to $C_3$) alkylene glycol-modified silicones that are hydrophobically modified with at least one alkyl substituent R having 4 to 20 carbon atoms in the molecule. The hydrophobic alkyl substituent R having 4 to 20 carbon atoms is preferably selected from n-butyl, n-pentyl, n-hexyl, n-heptyl, n-octyl, 2-ethylhexyl, n-decyl, n-undecyl, n-dodecyl, n-tetradecyl, n-hexadecyl=cetyl, n-octadecyl=stearyl, and n-eicosanyl=arachyl. The cetyl substituent is extraordinarily preferred.

Preferred ($C_2$ to $C_3$) alkylene glycols, with which the silicones are modified so that they acquire surface-active properties, are selected from ethylene glycol and propylene glycol. The desired emulsifier properties can be controlled by way of the weight ratio of ethylene-glycol and propylene-glycol units.

Particularly preferred silicone-based water-in-oil emulsifiers are selected from Cetyl PEG/PPG-10/1 Dimethicone (formerly Cetyl Dimethicone Copolyol, obtainable as Abil EM 90), also preferably Cetyl PEG/PPG-7/3 Dimethicone (e.g. Hansa SW 3010 (CHT R. Betilich GmbH)), PEG/PPG-10/3 Oleyl Ether Dimethicone, Lauryl Dimethicone PEG-15 Crosspolymer, Cetyl PEG/PPG-15/15 Butyl Ether Dimethicone (e.g. Wacker-Belsil DMC 3071 VP), and Lauryl PEG/PPG-18/18 Methicone (e.g. Dow Corning 5200 Formulation Aid of Dow Corning). Cetyl PEG/PPG-10/1 Dimethicone is extraordinarily preferred.

Preferred compositions according to the present invention are characterized in that the at least one silicone-based water-in-oil emulsifier having at least one alkyl substituent R having 4 to 20 carbon atoms is contained in a total quantity from 1 to 4 wt %, preferably 1.5 to 3.5 wt %, particularly preferably 2 to 3 wt %, extraordinarily preferably 2.2 to 2.5 wt %, based in each case on the total weight of the composition.

Further perspiration-inhibiting compositions preferred according to the present invention are characterized in that Cetyl PEG/PPG-10/1 Dimethicone is contained in a total quantity from 1 to 4 wt %, preferably 1.5 to 3.5 wt %, particularly preferably 2 to 3 wt %, extraordinarily preferably 2.2 to 2.5 wt %, based in each case on the total weight of the composition. Further perspiration-inhibiting compositions preferred according to the present invention are characterized in that Lauryl PEG/PPG-18/18 Methicone is contained in a total quantity from 1 to 4 wt %, preferably 1.5 to 3.5 wt %, particularly preferably 2 to 3 wt %, extraordinarily preferably 2.2 to 2.5 wt %, based in each case on the total weight of the composition. Further perspiration-inhibiting compositions preferred according to the present invention are characterized in that Cetyl PEG/PPG-15/15 Butyl Ether Dimethicone is contained in a total quantity from 1 to 4 wt %, preferably 1.5 to 3.5 wt %, particularly preferably 2 to 3 wt %, extraordinarily preferably 2.2 to 2.5 wt %, based in each case on the total weight of the composition. Further perspiration-inhibiting compositions preferred according to the present invention are characterized in that Cetyl PEG/PPG-7/3 Butyl Ether Dimethicone is contained in a total quantity from 1 to 4 wt %, preferably 1.5 to 3.5 wt %, particularly preferably 2 to 3 wt %, extraordinarily preferably 2.2 to 2.5 wt %, based in each case on the total weight of the composition.

Further perspiration-inhibiting compositions preferred according to the present invention are characterized in that Cetyl PEG/PPG-10/1 Dimethicone and PPG-3 myristyl ether are contained. Further perspiration-inhibiting compositions preferred according to the present invention are characterized in that Cetyl PEG/PPG-10/1 Dimethicone is contained in a quantity from 1 to 4 wt %, preferably 1.5 to 3.5 wt %, particularly preferably 2 to 3 wt %, extraordinarily preferably 2.2 to 2.5 wt %, and PPG-3 myristyl ether in a quantity from 0.8 to 4 wt %, preferably 1 to 3 wt %, particularly preferably 2 to 2.5 wt %, based in each case on the total composition.

Further perspiration-inhibiting compositions preferred according to the present invention are characterized in that Lauryl PEG/PPG-18/18 Methicone and PPG-3 myristyl ether are contained. Further perspiration-inhibiting compositions preferred according to the present invention are characterized in that Lauryl PEG/PPG-18/18 Methicone is contained in a quantity from 1 to 4 wt %, preferably 1.5 to 3.5 wt %, particularly preferably 2 to 3 wt %, extraordinarily preferably 2.2 to 2.5 wt %, and PPG-3 myristyl ether in a quantity from 0.8 to 4 wt %, preferably 1 to 3 wt %, particularly preferably 2 to 2.5 wt %, based in each case on the total composition. Further perspiration-inhibiting compositions preferred according to the present invention are characterized in that Cetyl PEG/PPG-15/15 Butyl Ether Dimethicone and PPG-3 myristyl ether are contained. Further perspiration-inhibiting compositions preferred according to the present invention are characterized in that Cetyl PEG/PPG-15/15 Butyl Ether Dimethicone is contained in a quantity from 1 to 4 wt %, preferably 1.5 to 3.5 wt %, particularly preferably 2 to 3 wt %, extraordinarily preferably 2.2 to 2.5 wt %, and PPG-3 myristyl ether in a quantity from 0.8 to 4 wt %, preferably 1 to 3 wt %, particularly preferably 2 to 2.5 wt %, based in each case on the total composition.

Further perspiration-inhibiting compositions preferred according to the present invention are characterized in that Cetyl PEG/PPG-7/3 Butyl Ether Dimethicone and PPG-3 myristyl ether are contained.

Further perspiration-inhibiting compositions preferred according to the present invention are characterized in that Cetyl PEG/PPG-7/3 Butyl Ether Dimethicone is contained in a quantity from 1 to 4 wt %, preferably 1.5 to 3.5 wt %, particularly preferably 2 to 3 wt %, extraordinarily preferably 2.2 to 2.5 wt %, and PPG-3 myristyl ether in a quantity from 0.8 to 4 wt %, preferably 1 to 3 wt %, particularly preferably 2 to 2.5 wt %, based in each case on the total composition.

In a further preferred embodiment of the invention, the weight ratio of silicone-based water-in-oil emulsifiers to addition products of 1 to 14, preferably 1 to 8 propylene oxide units with a monovalent $C_{3-16}$ alkanol is 0.5 to 2, preferably 0.75 to 1.67, particularly preferably 0.9 to 1.33, extraordinarily preferably 1.

Further perspiration-inhibiting compositions preferred according to the present invention are characterized in that Cetyl PEG/PPG-10/1 Dimethicone and PPG-3 myristyl ether are contained at a weight ratio from 0.5 to 2, preferably 0.75 to 1.67, particularly preferably 0.9 to 1.33, extraordinarily preferably 1. Further perspiration-inhibiting compositions preferred according to the present invention are characterized in that Lauryl PEG/PPG-18/18 Methicone and PPG-3 myristyl ether are contained at a weight ratio of 0.5 to 2, preferably of 0.75 to 1.67, particularly preferably of 0.9 to 1.33, extraordinarily preferably of 1.

Further perspiration-inhibiting compositions preferred according to the present invention are characterized in that Cetyl PEG/PPG-15/15 Butyl Ether Dimethicone and PPG-3 myristyl ether are contained at a weight ratio of 0.5 to 2, preferably of 0.75 to 1.67, particularly preferably of 0.9 to 1.33, extraordinarily preferably of 1.

Further perspiration-inhibiting compositions preferred according to the present invention are characterized in that Cetyl PEG/PPG-7/3 Butyl Ether Dimethicone and PPG-3 myristyl ether are contained at a weight ratio of 0.5 to 2, preferably of 0.75 to 1.67, particularly preferably of 0.9 to 1.33, extraordinarily preferably of 1.

In addition to the hydrophobically alkyl-modified silicone-based water-in-oil emulsifiers listed above, in a preferred embodiment of the invention the silicone-based water-in-oil emulsifiers contained can be those whose previous INCI name was Dimethicone Copolyol, having the current INCI names PEG-x Dimethicone (where x=2 to 20, preferably 3 to 17, particularly preferably 11 to 12), PEG/PPG a/b Dimethicone (where a and b, mutually independently, denote numbers from 2 to 30, preferably 3 to 30, and particularly preferably 12 to 20, in particular 14 to 18), Bis-PEG/PPG-c/d Dimethicone (where c and d, mutually independently, denote numbers from 10 to 25, preferably 14 to 20, and particularly preferably 14 to 16), and Bis-PEG/PPG-e/f PEG/PPG g/h Dimethicone (where e, f, g, and h, mutually independently, denote numbers from 10 to 20, preferably 14 to 18, and particularly preferably 16). PEG/PPG-18/18 Dimethicone, which is obtainable commercially in a 1:9 mixture with cyclomethicone as DC 3225 C or DC 5225 C, also PEG/PPG-25/25 Dimethicone, obtainable under the designation Wacker-Belsil DMC 6031 from the Wacker company, PEG/PPG-4/12 Dimethicone, which is obtainable under the designation Abil B 8852, Bis-PEG/PPG-14/14 Dimethicone, which is obtainable commercially in a mixture with cyclomethicone as Abil EM 97 (Goldschmidt), Bis-PEG/PPG-20/20 Dimethicone, which is obtainable under the designation Abil B 8832, PEG/PPG-5/3 Trisiloxane (Silsoft 305), and PEG/PPG-20/23 Dimethicone (Silsoft 430 and Silsoft 440), are particularly preferred.

The compositions according to the present invention are stable even without silicone-free water-in-oil emulsifiers, and are therefore free of them. It has in fact been found that certain silicone-free water-in-oil emulsifiers can negatively influence the active-substance release of the compositions according to the present invention. Examples of such silicone-free W/O emulsifiers excluded according to the present invention are selected from substances of the general formula A-O—(CHR$^1$—X—CHR$^2$—O—)$_a$-A', where A and A' represent identical or different hydrophobic organic residues, a represents a number from 1 to 100, by preference 2 to 60, in particular 5 to 40, X represents a single bond or the group —CHOR$^3$, R$^1$ and R$^2$ represent a hydrogen atom or a methyl group, and are selected so that the two residues do not simultaneously represent methyl, and R$^3$ represents a hydrogen atom or a branched or unbranched, saturated or unsaturated alkyl or acyl group having 1 to 20 carbon atoms. Further excluded silicone-free W/O emulsifiers are selected so that the residues A and A' are selected from the group of the branched and unbranched, saturated and unsaturated alkyl and acyl residues and hydroxyacyl residues having 10 to 30 carbon atoms, and further from the group of the hydroxyacyl groups connected to one another via ester functions according to the pattern: OOC—R"—CR"H—(OOC—R"—CR'H)$_b$—OOC—R"—CHR', where R' is selected from the group of the branched and unbranched alkyl groups having 1 to 20 carbon atoms and R" is selected from the group of the branched and unbranched alkylene groups having 1 to 20 carbon atoms, and b can assume values from 0 to 200.

Further excluded silicone-free W/O emulsifiers are selected from
(1) saturated alcohols having 8 to 24 carbon atoms, in particular having 16 to 22 carbon atoms, e.g. cetyl alcohol, stearyl alcohol, arachidyl alcohol, or behenyl alcohol, or mixtures of said alcohols such as those obtained from industrial hydrogenation of vegetable and animal fatty acids;
(2) ethoxylated alcohols and carboxylic acids having 8 to 24 carbon atoms, in particular having 16 to 22 carbon atoms, that have an HLB value from 1 to 8, e.g. Laureth-1 or Laureth-4;
(3) partial esters of a polyol having 3 to 6 carbon atoms with saturated and/or unsaturated, branched and/or unbranched fatty acids having 8 to 24, in particular 12 to 18 carbon atoms. Such partial esters are, for example, the monoglycerides of palmitic, stearic, and oleic acid, the sorbitan mono- and/or diesters, in particular those of myristic acid, palmitic acid, stearic acid, or of mixtures of said fatty acids. Also to be mentioned here are the monoesters of trimethylolpropane, erythritol, or pentaerythritol and saturated fatty acids having 14 to 22 carbon atoms. Also excluded are the industrial monoesters that are obtained by esterification of 1 mol polyol with 1 mol fatty acid, and a mixture of monoesters, diesters, triesters, and optionally unesterified polyol.
(4) Polyglycerol esters of saturated and/or unsaturated, branched and/or unbranched alkanecarboxylic acids having a chain length from 8 to 24, in particular 12 to 18 carbon atoms, having up to 10 glycerol units, by preference up to 3 glycerol units, and a degree of esterification from 1 to 10, by preference 1 to 5;
(5) mono- and/or polyglycerol ethers of saturated and/or unsaturated, branched and/or unbranched alcohols having a chain length from 8 to 30, in particular 12 to 18 carbon atoms, having up to 10 glycerol units, by preference up to 3 glycerol units, and a degree of etherification from 1 to 10, by preference from 1 to 5;
(6) propylene glycol esters of saturated and/or unsaturated, branched and/or unbranched alkanecarboxylic acids having a chain length from 8 to 24, in particular 12 to 18 carbon atoms;
(7) methyl glucose esters of saturated and/or unsaturated, branched and/or unbranched alkanecarboxylic acids having a chain length from 8 to 24, in particular 12 to 18 carbon atoms; and
(8) polyglycerol-methyl glucose esters of saturated and/or unsaturated, branched and/or unbranched alkanecarboxylic acids having a chain length from 8 to 24, in particular 12 to 18 carbon atoms.

Further examples of silicone-free W/O emulsifiers excluded according to the present invention are glyceryl lanolate, glyceryl monostearate, glyceryl distearate, glyceryl monoisostearate, glyceryl monomyristate, glyceryl monooleate, diglyceryl monostearate, glyceryl monolaurate, glyceryl monocaprinate, glyceryl monocaprylate, diglyceryl monoisostearate, diglyceryl diisostearate, propylene glycol monostearate, propylene glycol monolaurate, sorbitan monoisostearate, sorbitan monolaurate, sorbitan monocaprylate, sorbitan sesquistearate, sorbitan monoisooleate, sucrose distearate, cetyl alcohol, stearyl alcohol, arachidyl alcohol, behenyl alcohol, isobehenyl alcohol, 2-ethylhexylglyceryl ether, selachyl alcohol, chimyl alcohol, polyethylene glycol (2)stearyl ether (Steareth-2), glyceryl sorbitan stearate, polyglyceryl-4 isostearate, polyglyceryl-2 sesquiisostearate, PEG-7 hydrogenated castor oil, isostearyldiglyceryl succinate, PEG-5 cholesteryl ether, PEG-30 dipolyhydroxystearate, decaglyceryl heptaoleate, polyglyceryl-3 diisostearate, PEG-8 distearate, diglycerol dipolyhydroxystearate, glycerol isostearate, sorbitan isostearate, polyglyceryl-3 methyl glucose distearate, PEG-2 stearate, PEG-45/Dodecyl Glycol Copolymer, PEG-22/Dodecyl Glycol Copolymer, and Methoxy PEG-22/Dodecyl Glycol Copolymer.

Preferred compositions according to the present invention are characterized in that at least one polyethylene glycol ether of a linear or branched $C_{12}$ to $C_{22}$ alkanol with 20 to 150 ethylene oxide units is contained. These compounds are known as oil-in-water emulsifiers. It has been found, surprisingly, that the addition of such polyethylene glycol ethers of a linear or branched $C_{12}$ to $C_{22}$ alkanol with 20 to 150 ethylene oxide units, in combination with the other obligatory constituents of the compositions according to the present invention, results in greatly improved, faster active-substance release of the perspiration-inhibiting active substance. It was particularly surprising that by no means all oil-in-water emulsifiers exert this promoting effect on the compositions according to the present invention, not even those that fall within the same HLB value range as the polyethylene glycol ethers, preferred according to the present invention, of a linear or branched $C_{12}$ to $C_{22}$ alkanol with 20 to 150 ethylene oxide units. Without intending to be limited to this theory, it is presumed that certain oil-in-water emulsifiers have a disruptive influence on the water-in-oil structure of the emulsion. Disruptive emulsifiers of this kind are, according to the present invention, less or not at all suitable.

Particularly preferred compositions according to the present invention are characterized in that the at least one polyethylene glycol ether of a linear or branched $C_{12}$ to $C_{22}$ alkanol with 20 to 150 ethylene oxide units is selected from Laureth-20, Laureth-25, Laureth-30, Laureth-35, Laureth-40, Laureth-45, Laureth-50, Laureth-55, Laureth-60, Laureth-65, Laureth-70, Laureth-75, Laureth-80, Laureth-85, Laureth-90, Laureth-95, Laureth-100, Myristeth-20, Myristeth-25, Myristeth-30, Myristeth-35, Myristeth-40, Myristeth-45, Myristeth-50, Myristeth-55, Myristeth-60, Myristeth-65, Myristeth-70, Myristeth-75, Myristeth-80, Myristeth-85, Myristeth-90, Myristeth-95, Myristeth-100, Ceteth-20, Ceteth-25, Ceteth-30, Ceteth-35, Ceteth-40, Ceteth-45, Ceteth-50, Ceteth-55, Ceteth-60, Ceteth-65, Ceteth-70, Ceteth-75, Ceteth-80, Ceteth-85, Ceteth-90, Ceteth-95, Ceteth-100, Ceteth-110, Ceteth-120, Ceteth-130, Ceteth-140, Ceteth-150, Isoceteth-20, Isoceteth-25, Isoceteth-30, Isoceteth-35, Isoceteth-40, Isoceteth-45, Isoceteth-50, Isoceteth-55, Isoceteth-60, Isoceteth-65, Isoceteth-70, Isoceteth-75, Isoceteth-80, Isoceteth-85, Isoceteth-90, Isoceteth-95, Isoceteth-100, Isoceteth-110, Isoceteth-120, Isoceteth-130, Isoceteth-140, Isoceteth-150, Steareth-20, Steareth-25, Steareth-30, Steareth-35, Steareth-40, Steareth-45, Steareth-50, Steareth-55, Steareth-60, Steareth-65, Steareth-70, Steareth-75, Steareth-80, Steareth-85, Steareth-90, Steareth-95, Steareth-100, Steareth-110, Steareth-120, Steareth-130, Steareth-140, Steareth-150, Isosteareth-20, Isosteareth-25, Isosteareth-30, Isosteareth-35, Isosteareth-40, Isosteareth-45, Isosteareth-50, Isosteareth-55, Isosteareth-60, Isosteareth-65, Isosteareth-70, Isosteareth-75, Isosteareth-80, Isosteareth-85, Isosteareth-90, Isosteareth-95, Isosteareth-100, Isosteareth-110, Isosteareth-120, Isosteareth-130, Isosteareth-140, Isosteareth-150, Arachideth-20, Arachideth-25, Arachideth-30, Arachideth-35, Arachideth-40, Arachideth-45, Arachideth-50, Arachideth-55, Arachideth-60, Arachideth-65, Arachideth-70, Arachideth-75, Arachideth-80, Arachideth-85, Arachideth-90, Arachideth-95, Arachideth-100, Arachideth-110, Arachideth-120, Arachideth-130, Arachideth-140, Arachideth-150, Beheneth-20, Beheneth-25, Beheneth-30, Beheneth-35, Beheneth-40, Beheneth-45, Beheneth-50, Beheneth-55, Beheneth-60, Beheneth-65, Beheneth-70, Beheneth-75, Beheneth-80, Beheneth-85, Beheneth-90, Beheneth-95, Beheneth-100, Beheneth-110, Beheneth-120, Beheneth-130, Beheneth-140, Beheneth-150, and mixtures thereof. Steareth-100 is extraordinarily preferred.

Further particularly preferred compositions according to the present invention are characterized in that the at least one polyethylene glycol ether of a linear or branched $C_{12}$ to $C_{22}$ alkanol with 20 to 150 ethylene oxide units is contained in a total quantity from 1 to 3.5 wt %, preferably 1.5 to 3.0, particularly preferably 1.8 to 2.5 wt %, based in each case on the entire emulsion; a content of 1.9, 2.0, 2.1, 2.2, 2.3, and 2.4 wt % can also be preferred.

Further compositions preferred according to the present invention are characterized by a viscosity at 21° C. from 30,000 to 150,000 mPas, preferably 40,000 to 120,000 mPas, particularly preferably 50,000 to 100,000 mPas, and extraordinarily preferably 50,000 to 100,000 mPas.

The viscosity indications refer to measurements using a rotary viscometer of the Brookfield company, selecting the spindle and rotation speed recommended in the Brookfield company manual "More Solutions to Sticky Problems."

Using T-bar spindles and a Helipath: Table VIS-1: Brookfield model LV and HA viscometers; upper limit of optimum viscosity range for measurement with measurement parameters indicated (in mPas [milliPascal×second])

| Spindle/Unit | Shear rate (revolutions per minute, rpm) | T-A | T-B | T-C | T-D |
|---|---|---|---|---|---|
| LVT | 0.3 | 66,600 | 133,000 | 333,000 | 666,000 |
| LVT | 0.6 | 33,300 | 66,600 | 16,600 | 333,000 |
| LVT | 1.5 | 13,300 | 26,600 | 133,000 | 333,000 |
| LVT | 3 | 6,660 | 13,300 | 33,300 | 66,600 |
| LVT; LVF | 6 | 3,330 | 6,660 | 16,600 | 33,300 |
| LVT; LVF | 12 | 1,660 | 3,330 | 8,300 | 16,600 |
| HAT | 0.5 | 800,000 | 1,600,000 | 4,000,000 | 8,000,000 |
| HAT; HAF | 1 | 400,000 | 800,000 | 2,000,000 | 4,000,000 |
| HAF | 2 | 200,000 | 400,000 | 1,000,000 | 2,000,000 |
| HAT | 2.5 | 160,000 | 320,000 | 800,000 | 1,000,000 |
| HAT; HAF | 5 | 80,000 | 160,000 | 400,000 | 800,000 |

Table VIS-2: Brookfield model RV viscometer; upper limit of optimum viscosity range for measurement with measurement parameters indicated (in mPas [milliPascal×second])

| Spindle/Unit | Shear rate (revolutions per minute, rpm) | T-A | T-B | T-C | T-D |
|---|---|---|---|---|---|
| RVT | 0.5 | 400,000 | 800,000 | 2,000,000 | 4,000,000 |
| RVT | 1.0 | 200,000 | 400,000 | 1,000,000 | 2,000,000 |
| RVT | 2.0 | 100,000 | 200,000 | 500,000 | 1,000,000 |
| RVF | 2.5 | 80,000 | 150,000 | 400,000 | 800,000 |
| RVF | 4 | 50,000 | 100,000 | 250,000 | 500,000 |
| RVT | 5 | 40,000 | 80,000 | 200,000 | 400,000 |

The viscosity indicated represents the upper limit value for the optimum measurement range for the respective spindle/rotation speed combination. If two different measurement parameter combinations are possible for a viscosity range, the spindle/rotation speed combination furnishing the higher scale value is selected. The viscosity indications furthermore refer to the composition 24 hours after manufacture and at a temperature of 21° C., measured with a Helipath.

Compositions preferred according to the present invention, having a preferred viscosity, are particularly well suited for application with a ball applicator or from a gel dispenser. In order to make the transparency of the composition evident to the consumer, a transparent package is preferred.

Further compositions preferred according to the present invention can contain additives such as deodorant active substances, UV filters, antioxidants, desensitizing active substances such as amino acids, proteins, and protein hydrolysates, vitamins and vitamin precursors, in particular panthenol, preservatives, antibacterial active substances, and perfumes and scents.

A further subject of the present Application is the non-therapeutic, cosmetic use of a perspiration-inhibiting composition to reduce and/or regulate perspiration and/or body odor.

With reference to further preferred embodiments of the use according to the present invention, the statements made regarding the compositions according to the present invention apply mutatis mutandis.

A further subject of the present Application is a non-therapeutic, cosmetic method for reducing and/or regulating perspiration and/or body odor, in which method a composition according to the present invention is applied onto the skin, preferably onto the skin in the axillary region.

A further subject of the present Application is a method for manufacturing a perspiration-inhibiting composition according to which the constituents of the hydrophobic oil phase, including the water-in-oil emulsifier(s) and the perfume, are mixed with one another; separately therefrom, the constituents of the hydrophilic phase, if applicable including the oil-in-water emulsifier(s), are mixed with one another; the refractive indices nD of the two phases are equalized with one another to a difference of +/−0.0005 at 25° C.; the water phase is slowly dripped into the oil phase with moderate stirring; and the mixture is homogenized.

With reference to further preferred embodiments of the method according to the present invention, the statements made regarding the compositions according to the present invention apply mutatis mutandis.

The Examples below are intended to illustrate the invention without limiting it thereto.

Transparent perspiration-inhibiting water-in-oil emulsion gels (all quantitative indications in wt %).

Examples 1, 2, and 2a are according to the present invention; Examples 3 to 9 are comparative examples not according to the present invention.

The perspiration-inhibiting compositions 1 to 9 were manufactured by mixing the constituents of the hydrophobic oil phase, including the water-in-oil emulsifier(s) and the perfume, with one another; separately therefrom, the constituents of the hydrophilic phase, if applicable including the oil-in-water emulsifier(s), were mixed with one another; the refractive indices nD of the two phases were equalized with one another to a difference of +/−0.0005 at 25° C.; the water phase was slowly dripped into the oil phase with moderate stirring; and the mixture was homogenized. All the Example compositions were highly transparent and exhibited good shelf stability (12 weeks at 40° C.).

These transparent perspiration-inhibiting water-in-oil emulsion gels were applied onto the skin in the axillary region using a transparent roll-on or gel dispenser.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

| | Example | | | | | | | | | |
|---|---|---|---|---|---|---|---|---|---|---|
| | 1 | 2 | 2a | 3 | 4 | 5 | 6 | 7 | 8 | 9 |
| Diethylhexyl carbonate | 12 | — | 13 | 14 | 14 | 5 | 13 | 12 | 14 | 14 |
| Di-(n-octyl) carbonate | — | 12 | — | — | — | — | — | — | — | — |
| $C_{10}$ to $C_{13}$ isoalkane | — | — | — | — | — | 9 | — | — | — | — |
| Cetyl PEG/PPG-10/1 Dimethicone | 2 | 2 | 2.5 | 2.5 | 2.5 | 2.5 | 2.5 | 2.5 | 2.5 | 2.5 |
| PPG-3 myristyl ether | 2 | 2 | 1 | — | — | — | 1 | — | — | — |
| Isolan GPS* | — | — | — | — | 0.25 | — | — | — | — | — |
| Softigen 767*** | — | — | — | — | — | — | — | 2 | — | — |
| Ethanol (96 vol %) | 5 | 5 | 5 | 5 | 5 | 5 | 5 | 5 | 5 | 5 |
| Perfume oil | 0.6 | 0.6 | 0.6 | 0.6 | 0.6 | 0.6 | 0.6 | 0.6 | 0.6 | 0.6 |
| Aluminum Zirconium Tetrachlorohydrex Gly (Non-activated), present as 46 wt % aqueous solution (quantitative indication per USP) | 8.3 | 8.3 | 8.3 | 9.7 | 8.3 | 8.3 | 8.3 | 8.3 | 8.3 | 8.3 |
| Aluminum Zirconium Tetrachlorohydrex Gly (Activated), present as a complex with 1,2-propylene glycol, solubilized in 1,2-propylene glycol (quantitative indication per USP) | 8.1 | 8.1 | 8.1 | 7.3 | 8.1 | 8.1 | 8.1 | 8.1 | 8.1 | 8.1 |
| Glycine + sodium glycinate (from the two perspiration-inhibiting active substances) | 4.2 | 4.2 | 4.2 | 4.3 | 4.2 | 4.2 | 4.2 | 4.2 | 4.2 | 4.2 |
| 1,2-Propylene glycol | 24.4 | 24.4 | 24.4 | 21.8 | 24.4 | 24.4 | 24.4 | 24.4 | 24.4 | 24.4 |
| Dipropylene glycol | 13.4 | 13.4 | 11 | 17.9 | 16.8 | 13.4 | 16.9 | 15.0 | 10.9 | 11.4 |
| Steareth-100 | 2 | 2 | 2 | — | — | — | — | — | — | — |
| Antil 200** | — | — | — | — | — | 2 | — | — | — | — |
| PEG-100 stearate | — | — | — | — | — | — | — | — | 2 | — |
| PEG-150 stearate | — | — | — | — | — | — | — | — | — | 2 |
| Free water and molecularly bound water | to 100 | to 100 | to 100 | to 100 | to 100 | to 100 | to 100 | to 100 | to 100 | to 100 |
| Release of the perspiration-inhibiting active substance (slope of conductivity-time curve) Scale 1 to 5 (good to bad) | 2 | 2 | 1 | 5 | 3 | 3 | 3 | 4 | 4 | 4 |

*Isolan GPS (Evonik): INCI: Polyglyceryl-4 Diisostearate/Polyhydroxystearate/Sebacate
**Antil 200 (Evonik): INCI: PEG-200 Hydrogenated Glyceryl Palmitate, PEG-7 Glyceryl Cocoate
***Softigen 767 (Sasol): INCI: PEG-6 Caprylic/Capric Glycerides

What is claimed is:

1. A perspiration-inhibiting composition in the form of a water-in-oil emulsion, comprising:
   a) 10 to 20 wt % external oil phase, comprising:
      i) at least one symmetrical, asymmetrical, or cyclic ester of carbonic acid with linear or branched $C_6$ to $C_{22}$ alkanols,
      ii) at least one addition product of 1 to 14 propylene oxide units with mono- or polyvalent $C_{3-16}$ alkanols included at a total quantity from 0.8 to 4 wt % based on the entire composition, the addition product being selected from the group consisting of PPG-2 myristyl ether and PPG-3 myristyl ether, and
      iii) cyclomethicone in a total quantity from 0 to at most 3 wt %;
   b) 75 to 90 wt % dispersed aqueous phase, comprising:
      i) 20 to 60 wt % of at least one compound selected from water-soluble polyvalent $C_2$ to $C_9$ alkanols having 2 to 6 hydroxyl groups, and water-soluble polyethylene glycols having 3 to 20 ethylene oxide units, and
      ii) 5 to 40 wt % of at least one perspiration-inhibiting aluminum-zirconium compound;
   c) at least one silicone-based water-in-oil emulsifier having at least one alkyl substituent having 4 to 20 carbon atoms;
   d) no silicone-free water-in-oil emulsifier;
   e) at least one polyethylene glycol ether of a linear or branched $C_{12}$ to $C_{22}$ alkanol with 20 to 150 ethylene oxide units, the at least one polyethylene glycol ether comprising 1.8 to 2.5 wt. % steareth-100, and
   f) free and molecularly bound water in a total quantity from 5 to 40 wt %, the perspiration-inhibiting composition being transparent and having a viscosity ranging between 30,000 and 150,000 and a gel consistency,
      wherein all wt % indications are based on the total weight of the emulsion, and wherein at least 20 wt % of the at least one perspiration-inhibiting aluminum-zirconium compound, based on the total quantity of perspiration-inhibiting aluminum-zirconium compound, is solubilized in at least one compound selected from water-soluble polyvalent $C_2$ to $C_9$ alkanols having 2 to 6 hydroxyl groups and from water-soluble polyethylene glycols having 3 to 20 ethylene oxide units.

2. The perspiration-inhibiting composition according to claim 1, wherein 20 to 100 wt % of the at least one perspiration-inhibiting aluminum-zirconium compound is made up of at least one complex of a perspiration-inhibiting aluminum-zirconium compound with a polyvalent alcohol that contains 20 to 50 wt %, perspiration-inhibiting aluminum-zirconium compound and 2 to 16 wt % molecularly bound water, the remainder to make up 100 wt % being at least one compound selected from water-soluble polyvalent $C_2$ to $C_9$ alkanols having 2 to 6 hydroxyl groups and from water-soluble polyethylene glycols having 3 to 20 ethylene oxide units.

3. The perspiration-inhibiting composition according to claim 1, wherein the at least one perspiration-inhibiting aluminum-zirconium compound is activated.

4. The composition according to claim 1, wherein the at least one perspiration-inhibiting aluminum-zirconium compound is included in a total quantity of from 8 to 25 wt %, based on the active-substance content per US Pharmacopoeia (USP) in the entire composition.

5. The perspiration-inhibiting composition according to claim 1, wherein the silicone-based water-in-oil emulsifier is selected from poly-($C_2$ to $C_3$)-alkylene glycol-modified silicones that are hydrophobically modified with at least one alkyl substituent having 4 to 20 carbon atoms in the molecule.

6. The perspiration-inhibiting composition according to claim 1, wherein the silicone-based water-in-oil emulsifier is selected from Cetyl PEG/PPG-10/1 Dimethicone, Cetyl PEG/PPG-7/3 Dimethicone, PEG/PPG-10/3 Oleyl Ether Dimethicone, Lauryl Dimethicone PEG-15 Crosspolymer, Cetyl PEG/PPG-15/15 Butyl Ether Dimethicone, and Lauryl PEG/PPG-18/18 Methicone.

7. The composition according to claim 1, wherein the at least one silicone-based water-in-oil emulsifier having at least one alkyl substituent having 4 to 20 carbon atoms is included in a total quantity from 1 to 4 wt %, based in each case on the total weight of the composition.

8. The composition according to claim 1, wherein the hydrophobic oil phase, without accounting for any emulsifiers, is made up, at a proportion of at least 60 wt % of at least one symmetrical, asymmetrical, or cyclic ester of carbonic acid with linear or branched $C_6$ to $C_{22}$ alkanols.

9. The composition according to claim 1, wherein the at least one compound, selected from water-soluble polyvalent $C_2$ to $C_9$ alkanols having 2 to 6 hydroxyl groups and from water-soluble polyethylene glycols having 3 to 20 ethylene oxide units, is included at a total quantity of from 25 to 55 wt %, based on the total weight of the emulsion.

10. A non-therapeutic cosmetic method for reducing and/or regulating sweating and/or body odor, wherein a composition according to claim 1 is applied onto the skin.

* * * * *